United States Patent [19]

Teirstein

[11] Patent Number: 5,336,184
[45] Date of Patent: Aug. 9, 1994

[54] RAPID EXCHANGE CATHETER

[76] Inventor: Paul S. Teirstein, 402 Coast Blvd.,S., La Jolla, Calif. 92037

[21] Appl. No.: 92,332

[22] Filed: Jul. 15, 1993

[51] Int. Cl.⁵ .................... A61M 29/00; A61M 31/00
[52] U.S. Cl. .................... 604/102; 604/53; 606/194
[58] Field of Search ................ 128/656-658; 604/96-103; 606/192-194

[56] References Cited

U.S. PATENT DOCUMENTS

| | | | |
|---|---|---|---|
| 4,771,777 | 9/1988 | Horzewski et al. | 604/101 X |
| 4,819,751 | 4/1989 | Shimada et al. | 606/194 |
| 4,909,781 | 3/1990 | Husted | 606/194 |
| 4,944,745 | 7/1990 | Sogard et al. | 606/194 |
| 5,061,273 | 10/1991 | Yock | 604/96 |
| 5,135,535 | 8/1992 | Kramer | 604/102 X |
| 5,147,377 | 9/1992 | Sahota | 604/96 X |
| 5,154,725 | 10/1992 | Leopold | 604/96 X |
| 5,156,594 | 10/1992 | Keith | 604/96 |
| 5,171,222 | 12/1992 | Euteneuer et al. | 604/160 |
| 5,180,367 | 1/1993 | Kontos et al. | 604/101 |
| 5,205,822 | 4/1993 | Johnson et al. | 604/160 X |
| 5,232,445 | 8/1993 | Bonzel | 604/96 |

*Primary Examiner*—C. Fred Rosenbaum
*Assistant Examiner*—Frank Wilkens
*Attorney, Agent, or Firm*—Nydegger & Associates

[57] ABSTRACT

A novel over the wire-rapid exchange catheter is provided comprising a novel proximal end, which works in conjunction with the distal end of a traditional rapid exchange catheter, having a particular arrangement as shown in FIG. 1 which serves to enhance the users ability to properly operate and maneuver the guidewire/catheter, and thus to more effectively carry out the catherization procedure.

Additionally, an OTW-RE catheter is provided with a means for rapidly removing the guidewire from the proximal end of the catheter, at the appropriate time during the procedure, while preserving the integrity of the device.

13 Claims, 4 Drawing Sheets

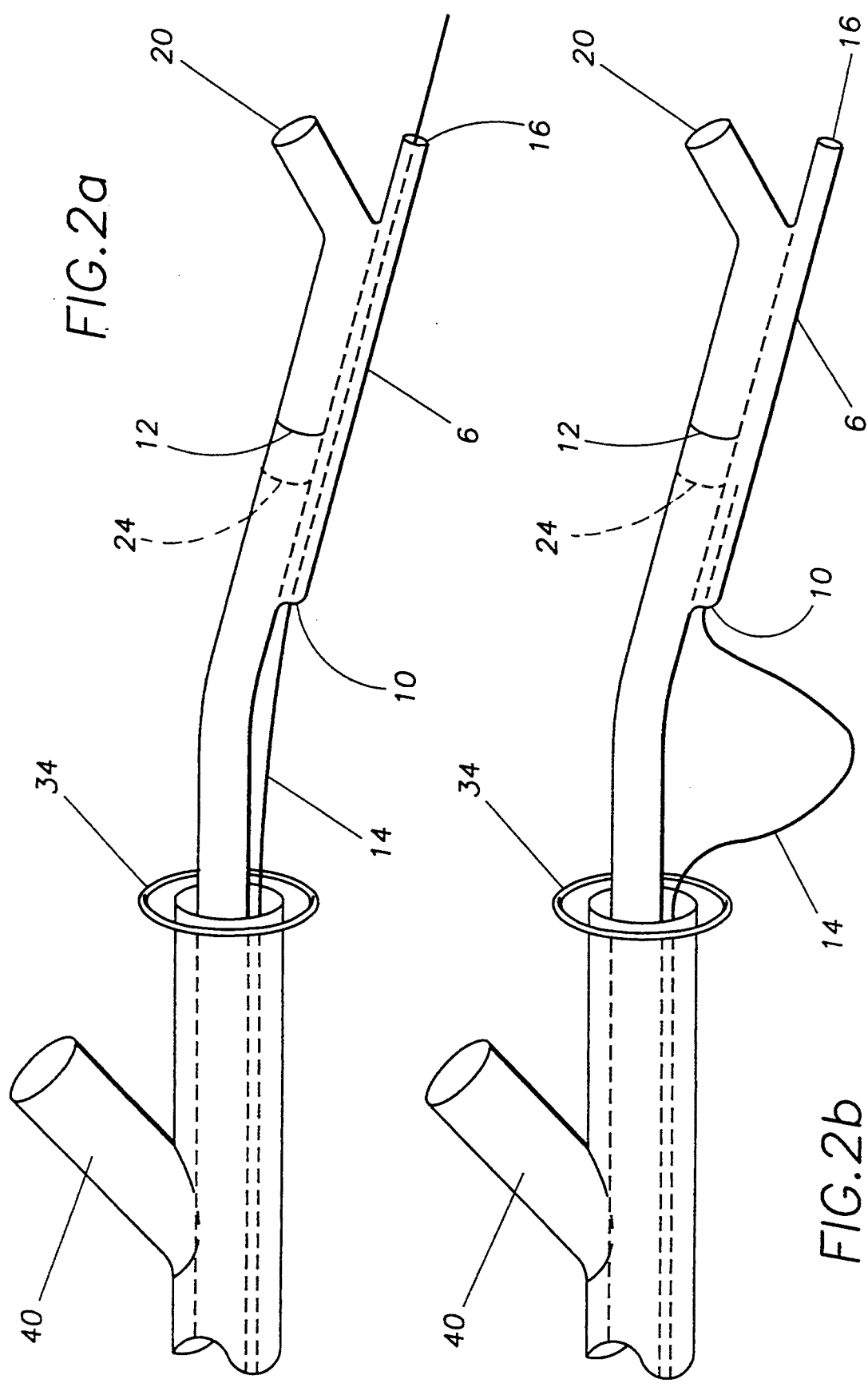

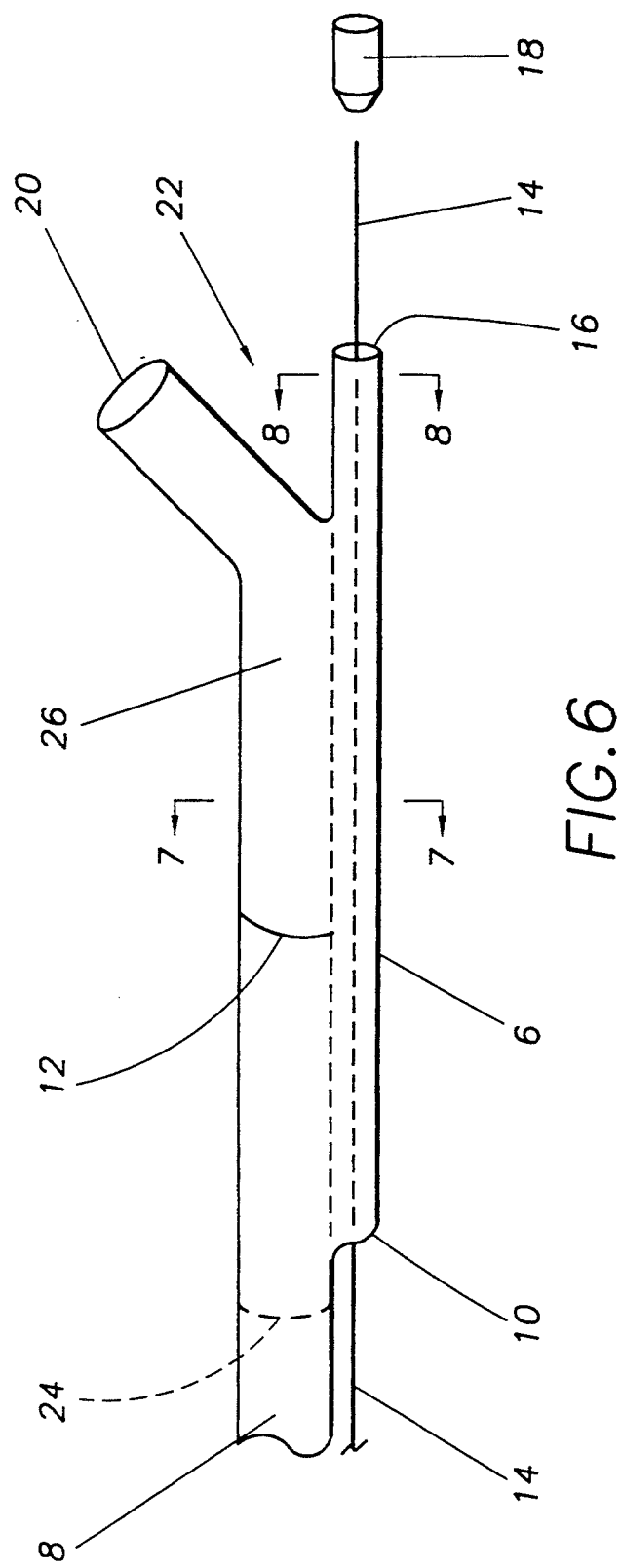
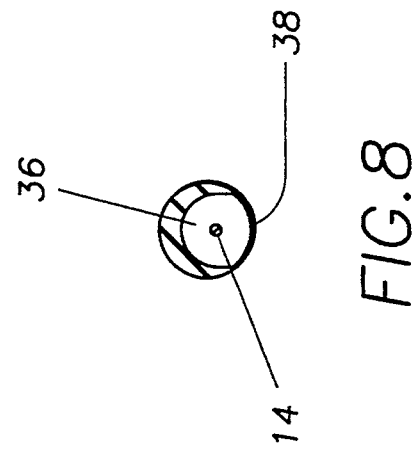
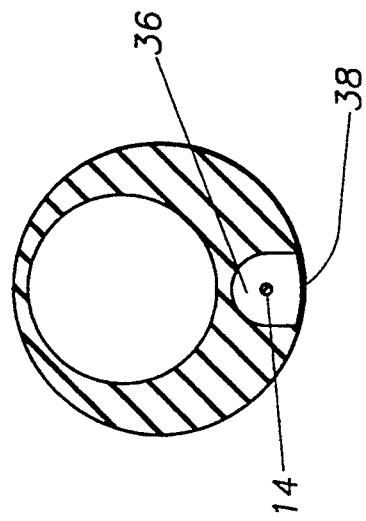

RAPID EXCHANGE CATHETER

BACKGROUND OF THE INVENTION

The present invention relates generally to the area of rapid exchange (RE) catheters and more particularly to the area of over the wire—rapid exchange (OTW-RE) catheters having a unique combination of specific features not heretofore available in known prior art devices.

From the perspective of "over-the-wire" (OTW) users, "rapid exchange" (RE) catheters pose several problems related to the requirement that the wire lies outside of the catheter body. There are two distinct techniques for introducing a traditional rapid exchange catheter into a coronary stenosis, each of which poses it's own set of problems.

In the first such technique (hereinafter referred to as Method I), the guidewire is first advanced across the lesion ("bare wired"). Then, the RE catheter is advanced over the guidewire into the lesion.

Various problems occur using Method I, which leads many OTW users to dislike "bare wiring".

Initially, a balloon catheter surrounding the wire often provides needed support when wiring tortuous arteries. For example, when two or more curves are present, it is often helpful to advance the wire through the first curve and then bring the balloon catheter over the wire into the first curve before attempting to wire through the second curve. This becomes a matter of instinct and habit for the OTW user, however, this technique is not possible to use when "bare wiring".

Secondly, contrast injections cannot be made simultaneously with "bare wire" advancement due to leakage of contrast around the "O" ring of the "Y" connector. This problem can be solved by using a wire introducer which fits into the "O" ring, however the use of such a wire introducer adds an additional step to the procedure.

Further, the two pieces of equipment, wire and catheter, must be threaded through the guiding catheter separately when using the bare wire technique; first, the wire and second, the catheter. OTW users have become accustomed to threading the catheter and wire together in one movement through the guiding catheter. This procedure is more efficient and serves to avoid wasted time and motion for the OTW user.

In the second prior art technique (Method II), the guidewire is first loaded into a traditional rapid exchange catheter, then the combined system is advanced to the coronary ostium, the "O" ring is then tightened partially, and then the guidewire is advanced through the lesion. This allows the catheter to support the guidewire. In tortuous arteries the catheter can be moved partly into the artery to support the advancing guidewire.

There are also problems which arise using this second technique.

First, it is difficult to coordinate the advancement of the catheter and wire through the guide catheter together because the guidewire lies outside of the catheter. The guidewire can easily slip out of the guide catheter during advancement.

Secondly, the guidewire's advancement to the lesion is cumbersome because the guidewire exits the "O" ring alongside the catheter. For dye injections the "O" ring must be tight, therefore, simultaneous dye injections and wire advancement become awkward, if not impossible. Furthermore, the guidewire movement is always impinged by the "O" ring and its normal exit position, which is off to one side, feels awkward to the operator.

The aforementioned disadvantages of the currently available prior art devices can be overcome, in large part, by employing the OTW-RE catheter arrangement described in the present invention.

Various prior art references exist, of which the applicant is currently aware, which refer generally to the area of catheter systems and which are related to the device of the present invention. The most important amongst these are:

Bonzel, U.S. Pat. No. 4,762,129, which issued on Aug. 9, 1988, and concerns a dilation catheter having a tube, the operative end of which opens into an expandable balloon, and a segment of flexible tubing traversing the balloon, sealingly connected to the distal end of the balloon, and capable of being threaded by a guidewire;

Yock, U.S. Pat. No. 5,040,548, which issued on Aug. 20, 1991, and relates to an apparatus for introduction into the vessel of a patient comprising a guiding catheter adapted to be inserted into the vessel of the patient and a device adapted to be inserted into the guiding catheter; and Kramer, U.S. Pat. No. 5,135,535, which issued on Aug. 4, 1992, teaches an intravascular catheter system, such as a dilatation catheter system for angioplasty procedures, which provides for the replacement of the catheter or the guidewire thereof during the procedure.

Scopton, et al, PCT Application No. WO 92/17236, relates to a catheter having a balloon at its distal most end, and having means for adjustably controlling the stiffness of the catheter shaft, and more particularly to a convertible-type balloon catheter having stiffener means disposed within the catheter. There is no teaching in this reference of any means for effecting the improvements taught by the inventor in the present application.

There are no other references of which the applicant is currently aware, which relate to the subject matter of the present invention.

None of the aforementioned prior art references teach an over the wire-rapid exchange catheter having the unique combination of specific features taught by the applicant in the present invention.

It is therefore an object of the present invention to provide an over the wire-rapid exchange catheter having a unique combination of characteristics not heretofore available in the prior art.

It is a further object of the present invention to provide an improved over the wire-rapid exchange catheter which serves to enhance the users ability to properly operate the guidewire/catheter and thus to allow the user to more expeditiously carry out the required catherization procedure.

It is another object of the present invention to provide a novel over the wire-rapid exchange catheter which allows the user the ability to rapidly separate the guidewire from the proximal guidewire channel of the catheter, as required during the procedure, in such a manner that the integrity of the OTW-RE catheter is preserved during the procedure, but which at the same time permits ease of removal of the guidewire from the proximal guidewire channel with a minimum of effort.

Lastly, it is an object of the present invention to provide an improved method for the operation of an over the wire-rapid exchange catheter using the improved device described herein.

These and other objects of the invention will be reflected in the course of the following discussion of the invention.

SUMMARY OF THE INVENTION

According to the present invention, there is provided a novel over the wire rapid-exchange catheter having a combination of unique advantages, not heretofore provided to users of available prior art catheters. The catheter of the present invention comprises a new proximal end, or back end, which works in conjunction with the distal end of any traditional rapid exchange catheter and serves to enhance the users ability to properly operate and maneuver the guidewire/catheter and thus to carry out the required catherization procedure.

Additionally, the OTW-RE catheter of the present invention provides for a means for rapidly separating the guidewire from the proximal guidewire channel of the catheter, at the appropriate time during the procedure, in a manner which serves both to preserve the integrity of the device prior to removal of the guidewire from the proximal guidewire channel and to allow ease of removal, once such is desired by the user, i.e. once the guidewire is no longer required for the procedure.

DESCRIPTION OF THE FIGURES

FIG. 2a) is a schematic representation of one phase of the typical operation of the OTW-RE catheter of the present invention.

FIG. 2b) is a schematic representation of another phase of the typical operation of the OTW-RE catheter of the present invention.

FIG. 6 is a schematic representation of an alternative embodiment of the OTW-RE catheter of the present invention showing the optional rupturable membrane for quick removal of the guidewire.

FIG. 7 is a cross section of the alternative embodiment of FIG. 6, at section "A".

FIG. 8 is a cross section of the alternative embodiment of FIG. 6, at section "B".

DETAILED DESCRIPTION OF THE INVENTION

The catheter of the present invention as described herein is an over the wire-rapid exchange (OTW-RE) catheter. Essentially, this catheter comprises of a new proximal or back end that works and can be used in conjunction with the distal end of any traditional RE catheter, such as for example a balloon catheter distal end, or other therapeutic catheter or diagnostic means.

Figure 1:
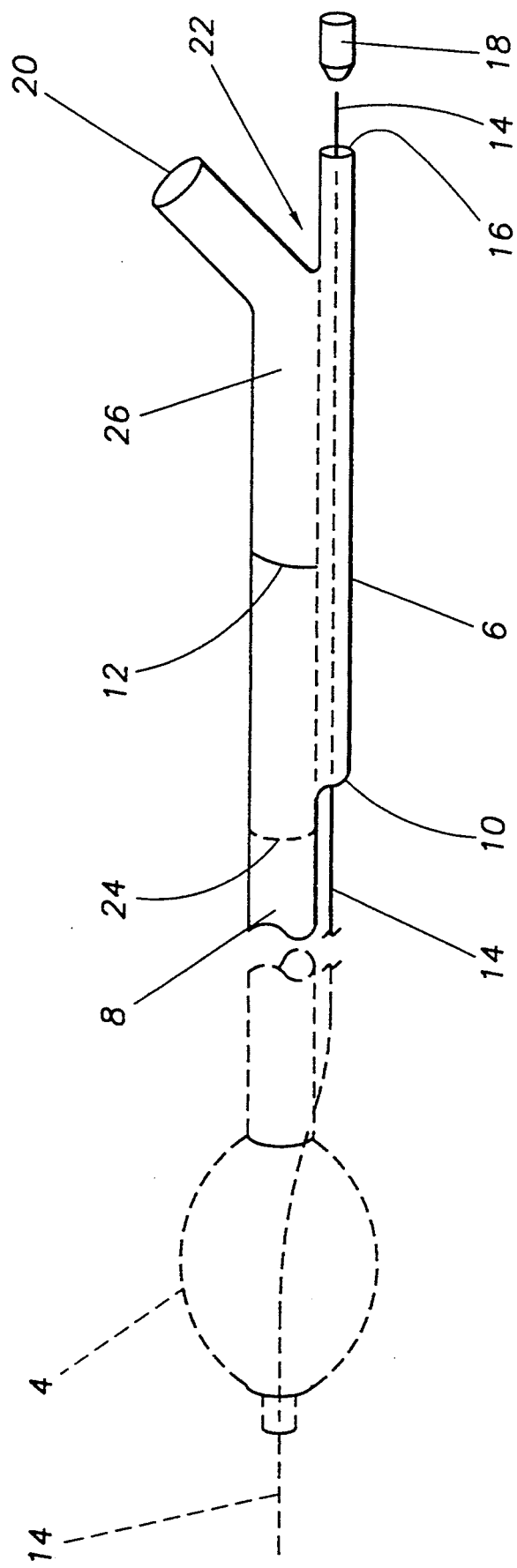
FIG. 1 is a schematic representation of the proximal end of one embodiment of the novel OTW-RE catheter of the present invention.

With reference to FIG. 1, which depicts the proximal end of a generally elongated catheter body 8, attached to a balloon catheter distal end 4, a wire re-entry port 10 is located in the end of a guidewire channel 6, which re-entry port is distal to the femoral marker 12. Here, the wire 14 re-enters the catheter body, travels through the wire re-entry channel, and then exits the channel at the back end of the catheter at port 16. A steering device 18 can be adapted to the guidewire to provide guidewire torque and advancement. A balloon inflation/deflation port 20 exits the catheter at an approximately 45 degree angle, such that the proximal end of the balloon catheter forms a "Y" shape 22 typical of traditional OTW balloon catheters.

The catheter system of the present invention is provided with a total of four guidewire ports. When provided with a balloon catheter distal end, the first port is located at the distal end of the balloon, a second port is located just proximal to the balloon or up to 50 cm proximal to the balloon in order to allow the guidewire to exit the elongated catheter body 8 and pass alongside the catheter, a third port-the re-entry port 10, to permit entry of the guidewire into the guidewire channel, and a fourth port 16 at the catheter's most proximal end, to allow exit of the wire.

As will be understood by one skilled in the art, the location of the re-entry port 10 is somewhat variable depending upon the intended use of the catheter. References made throughout this application to "brachial marker" or "femoral marker" are to be taken as points of reference only and not to imply that in all cases such "markers" actually physically exist as a mark or location on the device.

While the "brachial marker" and "femoral marker" may in fact be physically present and indeed, for the purposes of the present invention are preferably physically present on the catheter device as points of reference for the user, it will be understood that such marks are not provided in all prior art devices, and the user operates such devices where no markers physically exist using a combination of experience and preference, as to how far to insert and withdraw the catheter during any given procedure.

It is nonetheless intended that the device which is described and claimed in the present application will encompass those OTW-RE catheters which employ the number and relative location of wire ports taught here for the first time, even though the device may not have the location of the "brachial marker" and or "formal marker" physically indicated on the device itself.

The wire re-entry port 10 must be distal to the femoral marker 12. For brachial use, the wire re-entry port must also be distal to the brachial marker 24. However, if the re-entry port is distal to the brachial marker, it may be cumbersome to use the catheter by the femoral approach because the catheter will have to be withdrawn an extra distance to expose the wire re-entry port. Therefore, the catheter of the present invention requires two embodiments, one for femoral and one for brachial use, in each of which embodiments the re-entry port is located in one of the optional positions noted above.

As will be understood by one skilled in this art, all prior art guide catheters "Y" adapters, guidewires, balloon catheters and other therapeutic catheters or diagnostic catheter means are not manufactured to precisely the same lengths in each case, owing to variations in intended use and other requirements.

Therefore, it will be understood that the measurements provided herein, while precise for the specified use and the typical situation indicated herein, are not intended to be limiting, but rather intended to provide relative locations for the general application of the improvements provided for by the present invention.

Given the typical prior art guide catheter length of approximately 106 cm, a "Y" adaptor length of approximately 7 cm, a typical guidewire length of approximately 180 cm, an overall balloon catheter length of approximately 145 cm and the requirement for the guidewire to extend approximately 10-30 cm into the coronary artery; for femoral use, the guidewire re-entry port 10 must be located at a distance of between about 32 cm and 57 cm from the proximal end of the catheter 16, allowing for about 10 to 35 cm of guidewire to extend into the coronary artery, whereas for brachial use, the re-entry port 10 must be located about 51-57 cm from the proximal end of the catheter 16, which will allow approximately 10-16 cm of guidewire to extend into the coronary artery.

Figure 5:
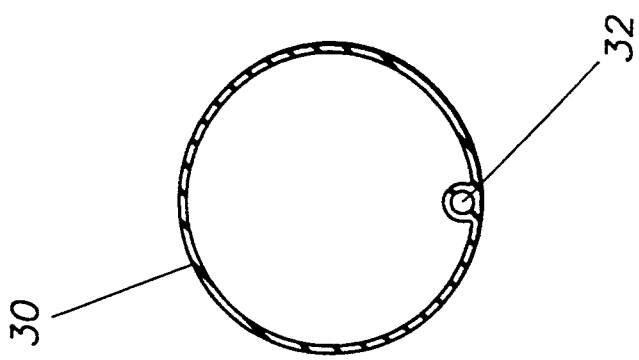
FIG. 5 is yet another schematic representation of a cross section of the proximal end of the catheter of the present invention depicting still another location of the guidewire.
Figure 4:
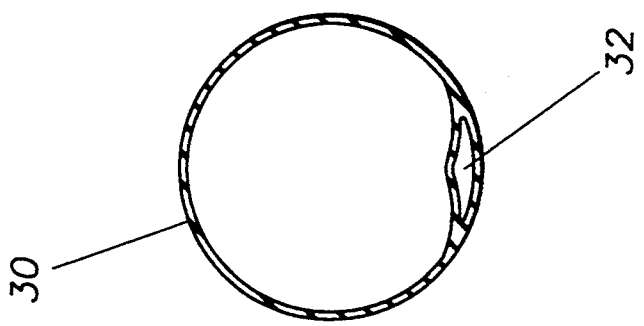
FIG. 4 is another schematic representation of a cross section of the proximal end of the catheter of the present invention depicting another possible location of the guidewire.
Figure 3:
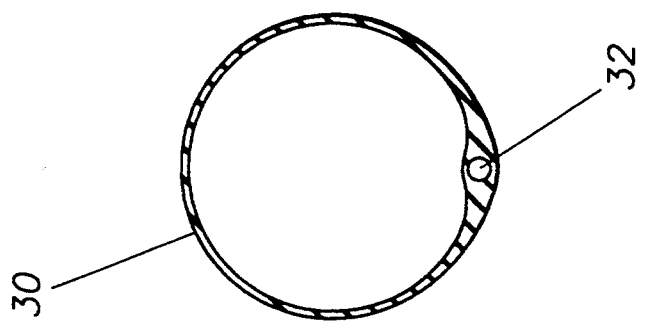
FIG. 3 is a schematic representation of a cross section of the proximal end of the catheter of the present invention depicting one possible location of the guidewire.

The proximal end catheter body 26 must be relatively round in cross section to allow the "O" ring to seal around it. This may be accomplished in any one of a number of optional ways, each of which is contemplated by the present invention, such as for example:

With reference to FIG. 3 where the catheter body is shown as being "built up" surrounding the inflation/deflation channel 30 and the wire re-entry channel 32, to approach a rounded shape; or, With reference to FIG. 4 where the balloon inflation/deflation channel 30 is indented to accommodate the wire re-entry channel 32; or, With reference to FIG. 5 where the wire re-entry channel 32 is placed within the balloon inflation/deflation channel 30.

With reference to FIGS. 2a) and 2b), in a typical procedure, although the user could start by loading the wire into the catheter (load the distal and the proximal end separately), the concept of the present invention functions better if the product is packaged with the wire pre-loaded. The user would then advance the OTW-RE catheter through a guide catheter 40 until the femoral marker on the OTW-RE catheter is reached. The user then tightens the "O" ring 34 around the femoral marker. The lesion is then crossed with a guidewire in the typical fashion of an over-the-wire catheter. That is, with simultaneous dye injections, which are easily achieved. The balloon catheter can be advanced partly into the artery to support the wire segment in regions of tortuosity where required. Thus, the catheter system of the present invention would be used in exactly the same manner as an existing prior art OTW catheter system. After balloon dilatation, to exchange the catheter, the device is withdrawn so that the wire entrance port 10 is exposed. The "O" ring is then tightened to prevent the device from slipping out of the coronary artery. The catheter is then flexed so that the wire and catheter separately slightly.

The torque device is removed from the wire, and the operator then pulls the wire backward so that it is removed from the wire re-entry channel. At this point, the catheter can be exchanged in the same manner as any traditional RE catheter.

With reference to FIGS. 6, 7 and 8, an alternative embodiment of the present invention is shown. In this embodiment, the wire re-entry port 10 leads to a channel shown in FIG. 7 in cross-section as 36. A portion of this channel is bordered by a rupturable membrane 38. The guidewire 14 can be removed from the guidewire re-entry channel by pulling the guidewire down at the back proximal end of the catheter 16. Pulling the guidewire down serves to sever the rupturable membrane and will allow separation of the guidewire from the proximal end of the balloon catheter. This obviates the need to bend the catheter and withdraw the guidewire through the re-entry channel port.

It should be noted that the embodiment of the present invention depicted in FIGS. 6, 7 and 8 is an improvement over a simple slit in the guidewire channel 36. A preformed slit allows dye to exit from the guidewire channel 36 during guiding dye injections. The rupturable membrane 38 of the present invention overcomes many of the problems which one might encounter with a pre-formed slit. First, if the "O" ring is tightened over the catheter, a slit may allow compression of the guidewire channel 36. Second, guiding injections of dye could easily leak through the "O" ring and out of a slit. Third, if the plunger on the contrast injection syringe is withdrawn, air could easily enter the catheter through such a slit.

Several preferred embodiments of the invention have been illustrated and various alternative arrangements have been described which will be effective to achieve the objectives set forth. Other alternative constructions and arrangements, including changes, modifications and substitution of parts, may be made, as will be obvious to those skilled in the art, without departing from the spirit of the invention.

I claim:

1. An improved over the wire rapid exchange catheter having a generally elongated catheter body with a proximal end and a distal end, a first guidewire port at said distal end where the guidewire enters said catheter body, and a second guidewire port spaced proximally from said distal end where the guidewire exits said catheter body, the improvement comprising:
   a reference marker affixed to said catheter body near said proximal end;
   an elongated guidewire channel formed on said catheter body near said proximal end;
   a third guidewire port formed in said proximal guidewire channel where the guidewire enters said proximal guidewire channel distal to said reference marker; and
   a fourth guidewire port formed in said proximal guidewire channel where the guidewire exits said proximal guidewire channel at the extreme proximal end of said elongated catheter body.

2. An over the wire-rapid exchange catheter according to claim 1, wherein the distal end of the catheter is a balloon or other therapeutic or diagnostic means.

3. An over the wire-rapid exchange catheter according to claim 1, wherein the distal end of the catheter is a balloon means, having a guidewire port at the distal end of the balloon.

4. An over the wire-rapid exchange catheter according to claim 1, having an overall length of 145 cm, wherein the distal end of the catheter is a balloon or other therapeutic or diagnostic means and the catheter is provided with a minimum of four distinct guidewire ports, said four ports being a guidewire entry port at the distal end of the catheter, a guidewire exit port located within 50 cm of the distal end of the catheter, a guidewire re-entry port located between 32-57 cm from the proximal end of the catheter, and a guidewire exit port at the extreme proximal end of the catheter body.

5. An over the wire-rapid exchange catheter according to claim 1 having a proximal end, wherein the elongated catheter body and proximal guidewire channel are formed in such a manner as to create a generally rounded or oval cross section.

6. An over the wire-rapid exchange catheter according to claim 1 having a proximal end, wherein the elongated catheter body is indented to form a portion of the proximal guidewire channel.

7. An over the wire-rapid exchange catheter according to claim 1 having a proximal end, wherein the proximal guidewire channel is formed within the elongated catheter body.

8. An over the wire-rapid exchange catheter according to claim 1, wherein the distal end is a balloon or other therapeutic or diagnostic means, and wherein the guidewire re-entry port is located at a distance of from about 32 to 57 cm from the proximal end of the catheter.

9. An over the wire-rapid exchange catheter according to claim 1, wherein the distal end is a balloon or other therapeutic or diagnostic means wherein the guidewire re-entry port is located about 51-57 cm from the proximal end of the catheter.

10. An over the wire-rapid exchange catheter according to claim 1, wherein the guidewire channel incorporated into the proximal end thereof is provided with a rupturable membrane which forms at least a portion of the outer wall of said guidewire channel.

11. An over the wire-rapid exchange catheter according to claim 1, wherein the proximal guidewire channel is incorporated into the outer wall of the elongated catheter body in order to form a generally rounded cross section shape, wherein the outer wall of the said guidewire channel is provided with a rupturable membrane which forms at least a portion of the said outer wall and runs the length of the said guidewire channel.

12. A method of using an OTW-RE catheter, comprising the steps of:

providing a guide catheter inserted into a patient to a selected location, said guide catheter having a selectively sealable "O" ring for sealing a proximal end of said guide catheter;

providing an OTW-RE catheter having a balloon or other therapeutic or diagnostic distal end, having a distal end of a guidewire threaded through a distal portion of the body of said OTW-RE catheter, having said guidewire exiting said distal portion of said catheter body, having an intermediate portion of said guidewire passing alongside said catheter body from said distal portion to a guidewire entrance port on a guidewire channel formed on a proximal portion of said catheter body where said guidewire re-enters said catheter body, and having a proximal end of said guidewire exiting said proximal guidewire channel;

providing a reference marker on said catheter body at a selected location to demonstrate appropriate length of insertion of said catheter body into the patient;

providing a torque device attached to said proximal end of said guidewire;

advancing said OTW-RE catheter through said guide catheter until said reference marker on said OTW-RE catheter is reached;

tightening said "O" ring around said reference marker;

advancing said guidewire to a selected treatment location with the simultaneous injection of contrast dye;

advancing said OTW-RE catheter as required to support said guidewire in regions of tortuosity;

dilating by inflating said balloon or effecting another therapeutic or diagnostic means;

subsequently withdrawing said OTW-RE catheter so that said guidewire entrance port is exposed;

tightening said "O" ring to prevent further movement of said OTW-RE catheter;

flexing said catheter body so that said guidewire separates slightly from said catheter body;

removing said torque device from said guidewire;

pulling on said guidewire until it is removed from said proximal guidewire channel; and exchanging said OTW-RE catheter in the conventional rapid exchange manner.

13. A method of using an OTW-RE catheter according to claim 12, further comprising the step of providing a rupturable membrane in an outer wall of said proximal guidewire channel, wherein the step of pulling on said guidewire removes said guidewire from said proximal guidewire channel by severing said rupturable membrane which forms a portion of said outer wall of said guidewire channel.

* * * * *